US012774272B2

(12) United States Patent
Sui

(10) Patent No.: US 12,774,272 B2
(45) Date of Patent: Oct. 27, 2026

(54) METHOD AND DEVICE FOR THE PRODUCTION OF LACTIDE

(71) Applicant: POLYWIN PTE. LTD., Singapore (SG)

(72) Inventor: Jianjun Sui, Singapore (SG)

(73) Assignee: POLYWIN PTE. LTD., Singapore (SG)

( * ) Notice: Subject to any disclaimer, the term of this patent is extended or adjusted under 35 U.S.C. 154(b) by 550 days.

(21) Appl. No.: 18/547,433

(22) PCT Filed: Feb. 22, 2021

(86) PCT No.: PCT/SG2021/050083

§ 371 (c)(1),
(2) Date: Aug. 22, 2023

(87) PCT Pub. No.: WO2022/177500

PCT Pub. Date: Aug. 25, 2022

(65) Prior Publication Data

US 2024/0140928 A1 May 2, 2024

(51) Int. Cl.

*B01D 3/14* (2006.01)
*B01D 3/00* (2006.01)

(Continued)

(52) U.S. Cl.

CPC ........... *C07D 319/12* (2013.01); *B01D 3/009* (2013.01); *B01D 3/148* (2013.01); *B01D 5/006* (2013.01)

(58) Field of Classification Search

CPC ........ B01D 3/009; B01D 3/148; B01D 5/006; C07D 319/12

See application file for complete search history.

(56) References Cited

U.S. PATENT DOCUMENTS 2,046,554 A * 7/1936 Gay ..................... B01D 5/0063 165/110
2,167,028 A * 7/1939 Mcgovern ............ B01D 5/0009 74/425

(Continued)

FOREIGN PATENT DOCUMENTS

WO 9315127 A1 8/1993

OTHER PUBLICATIONS

International Search Report from International Application No. PCT/SG2021/050083 mailed Nov. 4, 2021.

*Primary Examiner* — Jonathan Miller
(74) *Attorney, Agent, or Firm* — Shih IP Law Group, PLLC

(57) ABSTRACT

This invention relates to a method for the continuous production of optically pure lactide comprising a first reactive distillation system, a second reactive distillation system, a main distillation system and the side-draw refluxer. For each of the four systems a novel horizontally top-mounted condenser is used in order to decrease its total pressure drop and thus reduce side-reactions associated with high bottom temperature. In addition, a wiped film evaporator, a short path evaporator or a combination thereof is utilized for the concentration of the purge stream from the second reactive distillation, in a purpose of removing the metal contaminants contained in the purge stream and depolymerizing the contained unconverted lactic acid oligomers to crude lactide, all of which give additional advantages for the lactide production.

12 Claims, 2 Drawing Sheets

(51) Int. Cl.
*B01D 5/00* (2006.01)
*C07D 319/12* (2006.01)

(56) References Cited

U.S. PATENT DOCUMENTS

| | | | | | |
|---|---|---|---|---|---|
| 2,662,850 | A | | 12/1953 | Kraft | |
| 3,496,071 | A | * | 2/1970 | Spence | B01D 3/10<br>202/198 |
| 5,142,023 | A | * | 8/1992 | Gruber | C08G 63/08<br>525/415 |
| 5,247,059 | A | * | 9/1993 | Gruber | C08G 63/06<br>525/415 |
| 6,883,788 | B1 | * | 4/2005 | Tagamolila | B01D 3/166<br>165/DIG. 197 |
| 10,039,998 | B2 | * | 8/2018 | Zhang | B01D 3/148 |
| 2009/0301699 | A1 | * | 12/2009 | Karrs | F28F 9/22<br>165/159 |
| 2013/0240346 | A1 | * | 9/2013 | Zhang | B01D 3/148<br>202/189 |

* cited by examiner

METHOD AND DEVICE FOR THE PRODUCTION OF LACTIDE

BACKGROUND OF THE INVENTION

This invention relates to a method for the continuous production of optically pure lactide based on reactive distillation. The invention also relates to a device for producing lactide comprising a novel condenser causing a very low pressure drop during operation. In addition, a device is described for the concentration of the purge stream from the bottom of a second reactive distillation system. Likewise, purposes of use of both the devices and of the method are indicated.

Lactides are cyclic dimers of lactic acid and can be used as intermediates in the production of high molecular weight polylactic acid. These polymers are useful in the biomedical industry and other applications, for example as a decomposable packaging material due to their ability to be degraded biologically and hydrolytically while forming environmentally acceptable degradation products.

Examples of known methods for synthesizing lactide comprise a step of concentrating lactic acid as a raw material in an lactic acid concentrator to reduce the water content and facilitate the initiation of esterification between lactic acid molecules, a step of pre-polymerizing lactic acid in a prepolymer reactor to generate lactic acid oligomers during the removal of water resulting from esterification and a step of depolymerizing the thus obtained lactic acid oligomers to crude lactide in a depolymerization reactor. Methods for performing said concentration, pre-polymerization and depolymerization are known in the art, e.g., U.S. Pat. No. 6,326,458.

It is well known in the art that lactic acid includes two optical isomers, i.e., the (R)-lactic acid and (S)-lactic acid. Thus, formation of lactide from the enantiomers of lactic acid gives rise to three stereoisomers with different geometric structures distinguished as (R, R)-lactide (or D-lactide), (S, S)-lactide (or L-lactide) and (R, S)-lactide (or meso-lactide). In practice, a crude lactic acid feed to the system contains one of the two lactic acid selected from (S)-lactic acid and (R)-lactic acid as a major component. Therefore, the crude lactide produced by depolymerization contains a major portion of an optically pure lactide (L-lactide or D-lactide), a minor portion of meso-lactide and the remaining third lactide in an even much smaller amount.

While such a three-step method described in U.S. Pat. No. 6,326,458 allows to obtain crude lactide from an aqueous solution of lactic acid, one disadvantage of the process is the increased exposure of lactic acid to elevated temperatures as it is concentrated and pre-polymerized to the lactic acid oligomers. The starting lactic acid is usually of very high optical purity, with the (S)-lactic acid being more commercially available. However, some racemization occurs under those conditions, e.g., conversion of (S)-lactic acid as a major component to (R)-lactic acid, which results in a loss of the main product L-lactide and an increase in the amount of meso-lactide in the crude lactide. This can cause problems during the separation of meso-lactide from the optically pure lactide, for example L-lactide. An additional purification step may be required before the polymerization of L-lactide is performed.

In addition, as described in U.S. Pat. No. 6,326,458, the water vapors leaving the lactic acid concentrator and the prepolymer reactor are respectively condensed in two separated condensers, which water vapors inevitably carry over some lactic acid. The lactic acid carried over is preferably separated out from the condensates after the condensers and recycled back to the lactic acid concentrator or the prepolymer reactor. However, the recovery of the lactic acid from the condensates requires a great amount of thermal energy.

The above-mentioned disadvantages will be alleviated by replacing the two apparatus, i.e., the lactic acid concentrator and the prepolymer reactor by a single apparatus, i.e., a reactive distillation system to reduce the residence time of lactic acid and facilitate the separation of water from lactic acid. The reactive distillation system preferably comprises at least a pot, a distillation column, a condenser and an evaporator. The evaporator not only provides the energy required for the evaporation of water, but also is the place where the lactic acid condensation (pre-polymerization) reaction takes place. A concentration gradient is established within the distillation column with water being enriched in the rectifying section, and the higher-boiling point components such as lactic acid and lactic acid oligomers being enriched in the stripping section. The water contained in the aqueous solution of lactic acid and the water generated during the lactic acid condensation is distilled off as the overhead product stream, which stream consists essentially of water.

The introduction of the distillation column will increase the pressure drop of the reactive distillation system, which may result in the increase of the operating temperature in the associated evaporator and the pot. However, proper selection of suitable mass transfer elements for the distillation column will alleviate the problem. As a conventional condenser associated with the distillation column generally causes a pressure drop of about 5-20 mbar, it would be desirable to provide a condenser with a very low pressure drop to decrease the reaction temperature for the reactive distillation system and thus reduce the lactic acid racemization.

Similarly, a second reactive distillation system is proposed for the depolymerization reactor, which system comprises at least a pot, a distillation column, an evaporator and a condenser with a very low pressure drop.

The crude lactide from the second reactive distillation system not only comprises lactide but also other impurities, such as residual lactic acid, water, lactic acid oligomers and other reaction byproducts. The molecular weight of polylactic acid is controlled by the amount of hydroxylic impurities in lactide. In particular the presence of water, lactic acid and lactic acid oligomers in lactide tends to retard polymerization, and the resulting polylactic acid will not have a high molecular weight suitable for its use as a biodegradable polymer. It has been shown that the separation of the impurities from L-lactide can be achievable by means of distillation based on volatility differences between components. The relative order of decreasing volatility of the principal components in the crude lactide is water, lactic acid, meso-lactide, L-lactide and lactic acid dimers with boiling points at atmospheric pressure of about 100, 215, 250, 255 and 350° C., respectively, which boiling points are even higher for lactic acid trimers, tetramers, etc.

As described in U.S. Pat. No. 5,236,560, a crude lactide containing lactide, lactic acid, lactic acid oligomers and water is fed to a distillation column, wherein the purified lactide is withdrawn in the form of vapor from the side-draw of the distillation column. U.S. Pat. No. 8,569,517 proposes the separation of the crude lactide via a divided wall column, wherein the purified lactide in the form of liquid is obtained from the main fractionation zone at the other side of the divided wall.

While the purified lactide substantially free of lactic acid can be obtained from the distillation columns described in U.S. Pat. Nos. 5,236,560 and 8,569,517, it still contains a small amount of meso-lactide and lactic acid oligomers. Part of the lactic acid oligomers are formed due to the side reactions of lactic acid with lactide exposed to elevated temperature in the process of distillation. The residual lactic acid oligomers in the purified lactide have a negative impact on the polymerization rates, resulting in a relatively low molecular weight polylactic acid. In order to obtain virtually optically pure lactide, the purified lactide is subjected to a further purification step, e.g., melt crystallization. The residual meso-lactide can be easily separated from lactide by melt crystallization. However, it is difficult to remove the residual lactic acid oligomers from the lactide by melt crystallization as the lactic acid oligomers tend to be more viscous and stick to the surface of the lactide.

The above-mentioned problem will be overcome or at least alleviated by the introduction of a small column, i.e., a side-draw refluxer, which is connected downstream of the main distillation column with a vapor side-draw. The vapor side-draw stream withdrawn from the main distillation column is fed directly to the bottom of the side-draw refluxer with a top condenser, and the bottoms product from the side-draw refluxer is refluxed back to the main distillation column. The optically pure lactide stream substantially free of lactic acid and lactic acid oligomers is obtained at the top of the side-draw refluxer. Likewise, the main distillation column and the side-draw refluxer are separately equipped with a novel condenser with a low pressure drop caused during operation so as to reduce the bottom temperature of the main distillation column and the side reactions of lactic acid with lactide.

As crude lactide is generated, it is believed that some high-boiling or non-volatile contaminants present in the feed to the entire system will concentrate in the pot of the second reactive distillation system, including catalyst residues and metals built up due to the corrosion of the stainless-steel in the system. It is observed that the yield of the optically pure lactide is decreased in the lactide formation process over a period of time with no purge stream on the bottom of the pot in the second reactive distillation system, indicating that the metal contaminants are detrimental to the lactide generation and the inclusion of a purge stream is necessitated.

The purge stream is preferably not recycled back to the second reactive distillation system to prevent the accumulation of the metal contaminants. It would be desirable to provide a device for heating and concentration of the purge stream to recover the lactide by depolymerization of the lactic acid oligomers contained in the purge steam, while the bulk of the metals present in the purge stream can be removed and sent to a further process for the recovery of the metals by any well-known means.

SUMMARY OF THE INVENTION

It is an object of the present invention to develop a method and device for the production of optically pure lactide based on two reactive distillations and two conventional distillations, wherein a novel condenser is utilized for each distillation to decrease the total pressure drop, reduce the lactic acid racemization and the side reactions of lactic acid with lactide. The novel condenser is a horizontally top-mounted (HTM) condenser, which condenser is directed welded or connected to the top of each distillation column.

It is another object of the present invention to provide a method and device for the removal of the accumulated metal contaminants to increase the lactide generation in the second reactive distillation system. Specifically, the device comprises a wiped film evaporator, a short path evaporator or a combination thereof.

DETAILED DESCRIPTION OF THE PREFERRED EMBODIMENTS OF THE INVENTION

Figure 1:
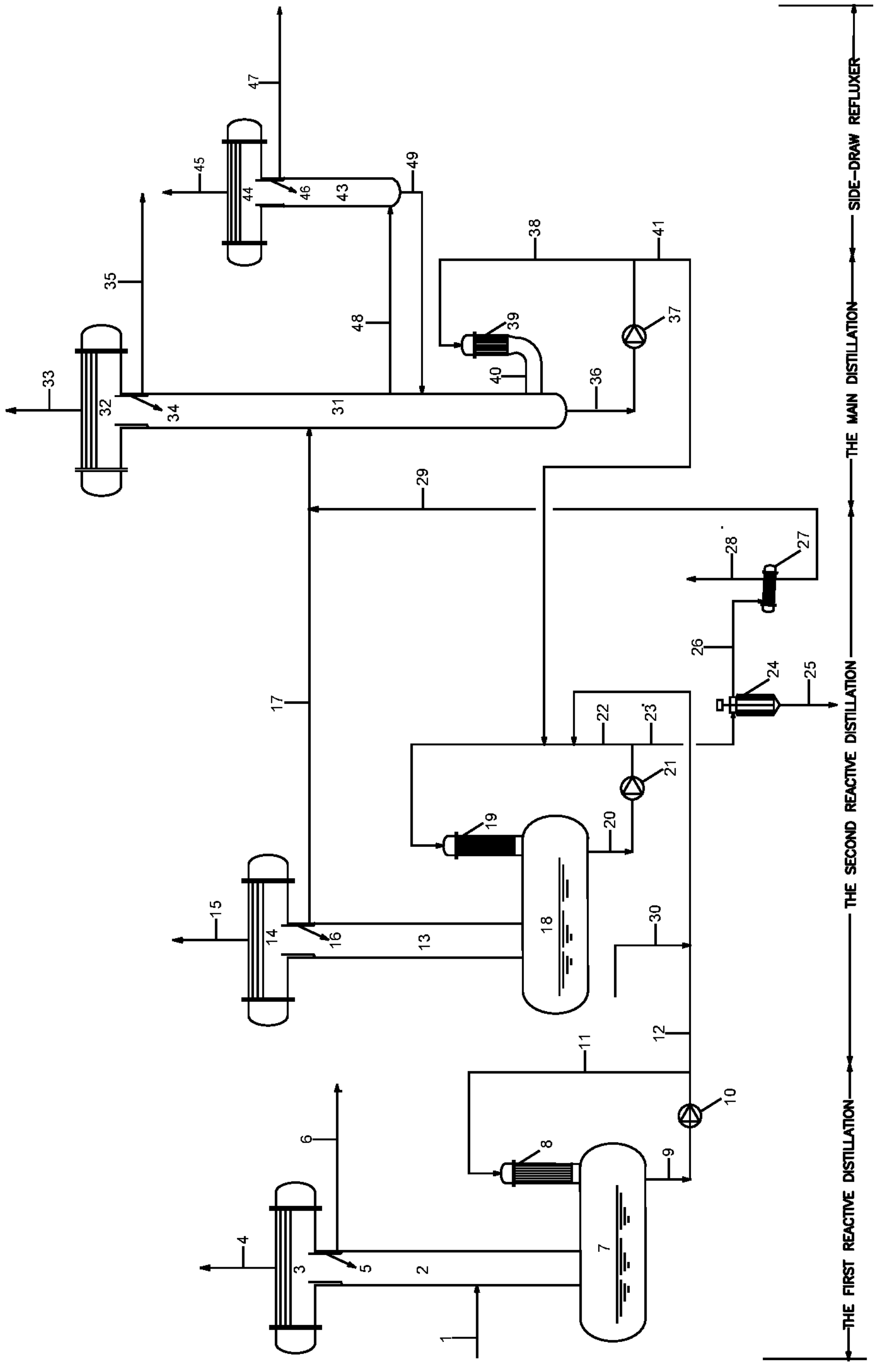
FIG. 1 is a schematic representation of a preferred lactide production system in accordance with the present invention.

With regard to the conventional reaction sequence, water contained in lactic acid is evaporated by heating in the lactic acid concentrator followed by a lactic acid condensation apparatus, wherein a lactic acid condensation (pre-polymerization) reaction is allowed to proceed for lactic acid oligomer generation. In accordance with the present invention, the two above-mentioned apparatus, i.e., the lactic acid concentrator and the prepolymer reactor are replaced by the first reactive distillation system. The expenditure on equipment and the space required for the installation of the first reactive distillation system are significantly decreased. Moreover, utilization of the first reactive distillation system has the advantages of decreasing the residence time of lactic acid, reducing the lactic acid racemization and thus increasing the yield of the optically pure lactide.

The aqueous solution of lactic acid as the feed can contain, for example, 0 to 50% by weight of water and 50 to 100% by weight of lactic acid, respectively. The temperature of the aqueous solution of lactic acid is preferably in the ranges of 60 to 150° C., and more preferably of 100 to 130° C.

In the first reactive distillation, the lactic acid concentration and lactic acid condensation reaction are allowed to proceed for the generation of lactic acid oligomers. The average molecular weight of the lactic acid oligomers obtained as a result of the lactic acid condensation reaction generally ranges from 300 to 10,000, preferably ranges from 450 to 5,000, and more preferably ranges from 600 to 2,500.

In accordance with the present invention, the first reactive distillation system preferably comprises at least a pot, a distillation column, a condenser and an evaporator. The orientation of the pot can be horizontal or vertical depending on the process conditions. The distillation column can be a conventional column or a divided wall column with a divided wall dividing the inner space of column. The evaporator not only provides the energy required for the evaporation of water, but also is the place where the lactic acid condensation reaction takes place.

The present invention is not particularly limited with regard to the type of mass transfer elements installed in the distillation column in the first reactive distillation system. Good results are obtained by using suitable mass transfer elements selected from the group consisting of trays, random packings, structured packings and any combinations thereof. It is however, structured packings are particularly suitable as mass transfer elements with the advantages of reducing the column pressure drop and liquid hold-up in the column. It is preferred that the structured packings have a specific surface area in the range of 50 to 750 $m^2/m^3$, and more preferably of in the range of 125 to 500 $m^2/m^3$.

The distillation column in the first reactive distillation system is equipped with at least one evaporator. The evaporator can be of any of the types commonly found in the chemical industry, including, but not limited to, falling film, forced circulation, thermosiphon and etc. However, due to its particularly reduced liquid hold-up and high heat transfer coefficient, a falling film evaporator is preferred to decrease the residence time of lactic acid and therefore reduce any unfavorable side-reactions, for example lactic acid racemization.

A conventional condenser is normally connected to the distillation column via connection elbows and pipes. Pressure drops ranging from 5-20 mbar are normally caused by a conventional condenser and its connecting pipes and fittings in the process of distillation. In order to facilitate the water removal and the condensation reaction between lactic acid molecules it would be desirable that the first reactive distillation is performed under a reduced pressure of 25 mbar or less. Most of the water vapors generated during operation are condensed in a condenser under deep vacuum attained by a vacuum system, for example at a preferred pressure of 20 mbar by making full use of chilled water as the cooling medium. Taking account of the pressure drops caused by the distillation column and the conventional condenser, the pressures at the pot and the evaporator will fall in the range of 30-45 mbar, which also indicates that the condensation reaction temperature in the evaporator will be higher than desired, leading to a relatively higher lactic acid racemization correspondingly.

Figure 2:
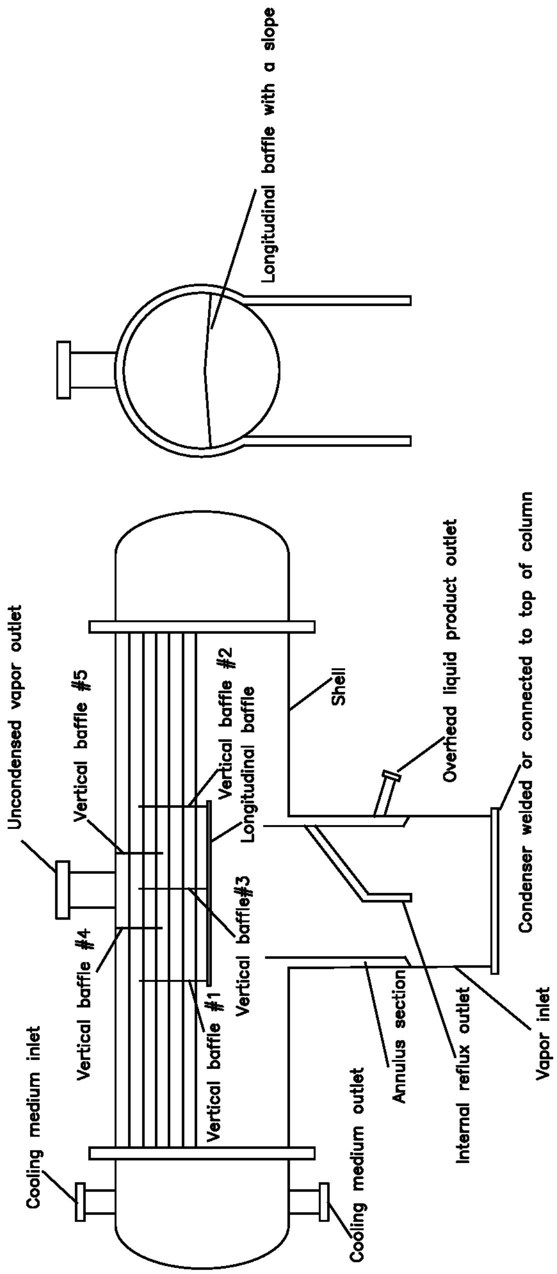
FIG. 2 is a schematic representation of a preferred HTM condenser in accordance with the present invention.

As shown in FIG. 2, the HTM condenser is a modified horizontal shell and tube heat exchanger, typically having one shell pass for the rising vapors from the top of the distillation column to be condensed and multiple tube passes preferably ranging from 2 to 8 for the cooling medium. The HTM condenser comprises a longitudinal baffle having a slope of approximately 3-7° installed in the middle of the shell, separating the inner space of the shell into a tube layout section above and an empty section below the baffle. In the tube layout section, two vertical single segmental baffles (baffle #1 and #2) are separately connected to the longitudinal baffle at the left and right end, with another three vertical single segmental baffles (baffle #3, #4 and #5) being installed in between them. The vapors from the top of the distillation column flowing upwards to the vapor inlet of the horizontally top-mounted HTM condenser are guided by the longitudinal baffle in two opposite directions, and then directed by the five vertical baffles for condensation. The vapor condensation takes place in the area created by the longitudinal baffle and the five vertical single segmental baffles by heat exchanging with the cooling medium flowing inside the tubes, and to a lesser extent in the area outside the left and right end of the longitudinal baffle. Most of the formed condensates flow across the sloped longitudinal baffle into the empty space of the shell through the gap between the longitudinal baffle and the inner wall of the shell, and the rest fall directly back to the empty space from outside the left and right end of the longitudinal baffle. All the condensates eventually are collected in the annulus section around the vapor inlet, which condensates are divided into an overhead liquid product stream distilled off from an outlet at a lower point of the annulus section and into an internal reflux stream taken from an outlet at a higher point feeding back to the top of the column. The uncondensed vapors are removed through the vapor outlet at the top of the HTM condenser.

Due to its particular geometric configuration, a pressure drop of less than 2 mbar can be realized during operation by a well-designed HTM condenser. It is therefore a HTM condenser is proposed in place of a conventional condenser for the condensation of the rising vapors from the top of the first reactive distillation system to minimize the operating pressures of the evaporator and the pot. In addition, an added advantage is that the expense for the installation of the HTM condenser is less as compared with the conventional condenser since fewer connection fittings and pipes are used.

In the first reactive distillation system, the distillation column with the horizontally top-mounted HTM condenser and the evaporator are preferably respectively mounted on top of the pot to create a single enclosed area within which lactic acid condensation and distillation take place. The aqueous solution of lactic acid is continuously fed to the inlet of the distillation column, which inlet is located at a point between the upper end and lower end of the column. The reaction solution enters at the top of the falling film evaporator, flows down the long vertical tubes which comprise the heat transfer and reaction zone, and exits at the bottom of the tubes in the form of vapor-liquid two-phase. The two-phase stream flows directly to the connected pot, wherein the vapor is disengaged from the liquid. The disengaged vapor flows upwards to the bottom of the top-mounted distillation column and the liquid is recovered in the pot. To prevent liquid film breakdown inside the tubes of the falling film evaporator the vaporization of the reaction solution is generally less than 15-30% by weight. A large portion of the liquid taken from the bottom of the pot as the reaction solution is recirculated via a transfer pump to the top of the falling film evaporator for continuous lactic acid condensation while a small portion thereof is fed to the subsequent depolymerization reactor. The reaction solution is heated in general at temperatures ranging from 120 to 200° C. and preferably ranging from 150 to 180° C.

In the process of the first reactive distillation, a concentration gradient is established within the column with water being enriched in the rectifying section, and the higher-boiling point components such as lactic acid and lactic acid oligomers being enriched in the stripping section. The water contained in the aqueous solution of lactic acid and the water generated during the lactic acid condensation is distilled off as the overhead vapor stream, which is condensed by the HTM condenser to obtain an internal reflux flowing downwards and an overhead product stream consisting essentially of water to be discarded. Vapors that have not been condensed in the HTM condenser are removed by a vacuum system. The high-boiling fraction consisting essentially of lactic acid and lactic acid oligomers liquefying within the column are allowed to flow back into the pot.

In accordance with the present invention, a second reactive distillation system is utilized for the depolymerization reactor, which system comprises at least a pot, a distillation column, a HTM condenser and a falling film evaporator. Similarly, the distillation column with the horizontally top-mounted HTM condenser and its associated falling film evaporator are respectively mounted directly on top of the pot to create a single enclosed area within which depolymerization and distillation take place. The structured packings are particularly suitable as mass transfer elements for the distillation column, having the advantages of reducing the column pressure drop and liquid hold-up in the column. It is preferred that the structured packings have a specific surface area in the range of 50 to 750 $m^2/m^3$, and more preferably of in the range of 125 to 500 $m^2/m^3$.

In the second reactive distillation, catalyst such as tin dioctoate is added and mixed with the lactic acid oligomers from the first reactive distillation, which mixture as part of the reaction solution is fed to the top of the falling film evaporator, wherein lactide is generated and vaporized. The vapor-liquid two-phase stream exits at the bottom of the tubes of the falling film evaporator and flows directly to the connected pot, wherein the vapor is disengaged from the liquid. The disengaged vapor flows upwards to the bottom of the top-mounted distillation column via the pot and the liquid is recovered in the pot. To prevent liquid film breakdown inside the tubes of the falling film evaporator the vaporization of the reaction solution is generally less than 15-30% by weight.

The reaction solution is heated in the evaporator at temperatures ranging from 120 to 250° C. and preferably ranging from 150 to 220° C. under reduced pressure of 100 mbar or less and preferably 10 mbar or less. An overhead low-boiling distillate stream, i.e., the crude lactide consisting of a major portion of L-lactide and some meso-lactide, lactic acid oligomer, residual water and lactic acid is formed, e.g., 60 to 99% by weight of L-lactide, 0 to 15% by weight of meso-lactide, 0 to 10% by weight of lactic acid, 0 to 12% by weight of lactic acid oligomers and 0 to 3% by weight of water. The high-boiling fraction consisting essentially of unconverted lactic acid oligomers flows back into the pot.

A large portion of the liquid taken from the bottom of the pot as part of the reaction solution is recirculated via a transfer pump to the top of the falling film evaporator for continuous depolymerization reaction while a small portion thereof is removed as the purge stream. The purge stream comprises a large portion of unconverted lactic acid oligomers and a small portion of high-boiling or non-volatile contaminants such as catalyst residues and metals built up due to the corrosion of the stainless-steel. It would be desirable to remove the bulk of the metals present in the purge stream while the unconverted lactic acid oligomers are depolymerized to crude lactide, which lactide are recovered and combined with the overhead product stream from the second reactive distillation for further purification.

According to a preferred embodiment of the invention, a wiped film evaporator is used for the concentration of the purge stream. A wiped film evaporator is also called a thin film or agitated thin film evaporator, which typically comprises a jacketed shell, an agitator, droplet separator and drive unit. The heating medium is flowing inside the heating jacket to provide the necessary thermal energy for depolymerization of the lactic acid oligomers in the purge stream and evaporation of the volatile components including the generated crude lactide. An agitator driven by the drive unit is provided with paddles, wipers or scrapers and arranged in the shell, so that the purge stream fed into the evaporator via the inlet is distributed uniformly as a film over the inner surface of the heating jacket. The vaporized components enter the droplet separator mounted on top of the shell so as to remove the entrained liquid before leaving the evaporator via the vapor outlet to an external condenser for condensation. The least volatile components including the residues of tin catalyst and metals contaminants are removed via the liquid outlet and sent to the subsequent process for the recovery of the metals.

Alternatively, taking account of the pressure drop of vapors flowing from the surface of the heating jacket to the external condenser, an internal condenser is arranged in the shell at a short distance from the surface of the heating jacket to reduce the pressure drop, so that in fact a short path evaporator is obtained.

The crude lactide from the second reactive distillation is fed to the subsequent main distillation column for the purification of L-lactide. The crude lactide is fractionated based on volatility differences between components. The relative order of decreasing volatility of the principal components in the crude lactide is water, lactic acid, meso-lactide, L-lactide and lactic acid oligomers. The less volatile components such as lactic acid oligomers, having a higher-boiling point than L-lactide, are concentrated at the bottom of the column and removed as bottoms product. The overhead product stream from the main distillation column contains a major portion of meso-lactide and a small portion of lactic acid and L-lactide. The lactide product with a high purity of L-lactide is withdrawn as the vapor side-draw from the main distillation column.

The overhead vapor stream at the top of the main distillation column is condensed by a HTM condenser to obtain a condensate stream enriched in meso-lactide. Vapors that have not been condensed in the condenser are removed by the vacuum system. A portion of the condensate stream is preferably refluxed into the column and the other portion is subjected to an additional purification system such as a distillation, a crystallization or a combination thereof to obtain pure meso-lactide.

The liquid bottom stream concentrated in the stripping section is drawn off from the bottom of the main distillation column and subsequently divided into a bottoms product stream and a recirculation stream. The increase of lactic acid oligomers content in the bottoms product stream is observed due to the side-reactions occurring between the lactide and the residual lactic acid under the condition of a relatively high bottom temperature. The bottoms product stream is preferably refluxed to the second reactive distillation system as part of the reaction solution for the depolymerization.

The lactide product stream taken off as the vapor side-draw of the main distillation column is substantially free of water and lactic acid. However, it still contains a small amount of lactic acid oligomers due to the side-reactions occurring between the lactide and the residual lactic acid in the process of distillation. The residual lactic acid oligomers in the lactide product stream are detrimental to the polymerization rates, resulting in a relatively low molecular weight polylactic acid.

In accordance with the present invention, the vapor side-draw stream of the main distillation column is fed directly to the bottom of the side-draw refluxer equipped with a HTM condenser, and the bottoms product from the side-draw refluxer is refluxed back to the main distillation column. In the side-draw refluxer, L-lactide is separated from the residual lactic acid oligomers and the purified L-lactide substantially free of lactic acid and lactic acid oligomers is obtained at the top of the side-draw refluxer.

The main distillation column and the side-draw refluxer are preferably carried out at low temperatures and reduced pressures. The pressure at the top of the main distillation column is preferably in the ranges of 3 to 25 mbar, and more preferably of 5 to 15 mbar. The pressure at the bottom of the main distillation column is preferably in the ranges of 10 to 35 mbar, more preferably of 12 to 25 mbar.

The mass transfer elements installed in the main distillation column and the side-draw refluxer consist of trays, random packings, structured packings and any combinations thereof. It is however, structured packings are particularly suitable as mass transfer elements with the advantages of reducing the column pressure drops and liquid hold-up. It is preferred that the structured packings have a specific surface area in the range of 125 to 750 $m^2/m^3$, and more preferably in the range of 250 to 350 $m^2/m^3$.

FIG. 1 schematically shows a preferred lactide production system in accordance with the present invention, which system comprises a column 2 of the first reactive distillation, a HTM condenser 3, a pot 7, a falling film evaporator 8, a pump 10, a column 13 of the second reactive distillation, a HTM condenser 14, a pot 18, a falling film evaporator 19, a pump 21, a wiped film evaporator 24, an external condenser 27, a main distillation column 31, a HTM condenser 32, a pump 37, a falling film evaporator 39, a side-draw refluxer 43 and a HTM condenser 44.

An aqueous solution of lactic acid is continuously fed through stream 1 to the first reactive distillation column 2. The overhead vapors consisting essentially of water are drawn off and subsequently condensed in the HTM condenser 3. The condensates are divided into an overhead liquid product stream 6 distilled off from the top, and into an internal reflux stream 5, which is fed back to the top of the distillation column 2. The uncondensed vapors are removed through stream 4. The lactic acid and the lactic acid oligomers are concentrated at the bottom of the column 2 and flow back to the pot 7. The bottom stream 9 taken from the bottom of the pot 7 is subsequently transferred via the pump 10 and divided into a bottoms product stream 12 and a recirculation stream 11, which recirculation stream is fed to the top of the falling film evaporator 8, partially vaporized and then flows to the pot 7. The vapors are disengaged from the liquid in the pot 7. The disengaged vapors flow upwards to the bottom of the column 2 and the liquid within the column 2 falls back to the pot 7.

The bottoms product stream 12 is mixed with the depolymerization catalyst stream 30, which mixture is combined with stream 22 and 41, and continuously fed to the top of the falling film evaporator 19. The overhead vapors containing a large portion of lactide are drawn off and subsequently condensed in the HTM condenser 14. The condensates are divided into an overhead liquid product stream 17 distilled off from the top, and into an internal reflux stream 16, which is fed back to the top of the distillation column 13. The uncondensed vapors are removed through stream 15. The unconverted lactic acid oligomers are concentrated at the bottom of the column 13 and flow back to the pot 18. The bottom stream 20 taken from the bottom of the pot 18 is subsequently transferred via the pump 21 and divided into a purge stream 23, and a recirculation stream 22. In the falling film evaporator 19, the liquid reaction solution is partially vaporized and then flows to the pot 18. The vapors are disengaged from the liquid in the pot 18. The disengaged vapors flow upwards to the bottom of the column 13 and the liquid within the column 13 falls back to the pot 18.

The purge stream 23 is fed to the inlet of the wiped film evaporator 24. The vapors generated from the wiped film evaporator 24 are subjected via stream 26 to condensation in the external condenser 27. The condensate from the condenser 27 is combined with the overhead product stream 17 and the uncondensed vapors are removed via stream 28. The least volatile components are removed from the wiped film evaporator 24 via stream 25.

The overhead product stream 17 from the distillation column 13 is fed to the main distillation column 31. The overhead vapors enriched in meso-lactide are drawn off and subsequently condensed in the HTM condenser 32. The condensates are divided into an overhead product stream 35 distilled off from the top of the main distillation column 31 and into an internal reflux stream 34, which is fed back to top of the main distillation column 31. The uncondensed vapors are removed through stream 33. The lactic acid oligomers are concentrated at the bottom of the main distillation column 31 and drawn off as a bottom stream 36. The bottom stream 36 is subsequently divided into a bottoms product stream 41 and a recirculation stream 38, which stream is fed to the inlet of the falling film evaporator 39, partially vaporized and then flows to the bottom of the main distillation column 31 via stream 40. The vapor side-draw stream 48 withdrawn from the main distillation column 31 is fed to the bottom of the side-draw refluxer 43. The overhead vapors in the side-draw refluxer 43 consisting essentially of L-lactide are drawn off and subsequently condensed in the HTM condenser 44. The condensates are divided into an overhead liquid product stream 47, and into an internal reflux stream 46, which is fed back to the top of side-draw refluxer 43. The uncondensed vapors are removed through stream 45. The bottoms product stream 49 from the side-draw refluxer 43 is refluxed to the main distillation column 31.

Subsequently, the present invention is illustrated in more details below with reference to the drawings and the examples.

EXAMPLES

Example 1

A distillation of the first reactive distillation system according to an embodiment of the invention as shown in FIG. 1 was performed. The distillation column 2 had a total of 9 theoretical stages. An aqueous solution of lactic acid stream 1 (90% by weight of lactic acid) with a mass flow rate of 4,600 kg/h at a temperature of 110° C. was continuously fed to the distillation column 2 with the feed inlet located at the point of theoretical stage 7. Structured packings with a specific surface area of 441 $m^2/m^3$ and 250 $m^2/m^3$ were used as mass exchange elements respectively for the rectifying section and stripping section of the distillation column 2. The falling film evaporator 8 heated the reaction solution up to a temperature of 180° C. The bottoms product stream 12 contained a major portion of lactic acid oligomers.

The HTM condenser 3 had a total of 815 tubes, each having a length of 4,500 mm and an outside diameter (OD) of 25.4 mm. The inner diameter (ID) of the shell of the HTM condenser 3 was 2,000 mm. The total surface area of the HTM condenser 3 was 282 $m^2$. The rising water vapors from the top of distillation column 2 were directly fed to the vapor inlet of the HTM condenser 3, wherein the condensation was performed by heat exchanging with the cooling medium flowing in the tubes. The condensates were collected in the annulus section around the vapor inlet, which condensates were divided into an overhead liquid product stream 6 distilled off at a lower point of the annulus section and into an internal reflux stream 5 feeding back to the top of the column 2. The uncondensed vapors stream 4 was removed through the vapor outlet at the top of the HTM condenser 3. The overhead product stream 6 with a mass flow rate of 1240 kg/h, consisting of substantially pure water, was removed for further water treatment. The pressure drops caused by the HTM condenser 3 and distillation column 2 were 1.9 mbar and 4.3 mbar, respectively, which pressure drops were added to give a total pressure drop of 6.2 mbar for the system. Setting the pressure of the vapor outlet stream 4 at 18.5 mbar by a vacuum system gave a pressure of 24.7 mbar for the evaporator 8 and the pot 7 during operation.

Example 2

A reactive distillation of the second reactive distillation system according to an embodiment of the invention as shown in FIG. 1 was performed. The distillation column 13 had a total of 6 theoretical stages. The bottoms product stream 12 from the first reactive distillation was mixed with the catalyst (tin dioctoate) stream 30 in a static mixer (not shown in FIG. 1) and combined with stream 22 and 41 to form a mixture of reaction solution, which mixture had a mass flow rate of 3,500 kg/h and was fed to the top of the falling film evaporator 19. Structured packings with a specific surface area of 125 $m^2/m^3$ were used as mass exchange elements for the distillation column 13. The crude lactide was distilled off while it was generated by the depolymerization of the lactic acid oligomers in the falling film evaporator 19, which evaporator heated the reaction solution up to a temperature of 215° C.

The HTM condenser 14 had a total of 605 tubes, each having a length of 4,000 mm and an OD of 19.05 mm. The shell ID of the HTM condenser 14 was 1,700 mm. The total surface area of the HTM condenser 14 was 139 $m^2$. The crude lactide vapors from the top of distillation column 13 were directly fed to the vapor inlet of the HTM condenser 14, wherein the condensation was performed by heat exchanging with the cooling medium flowing in the tubes. The condensates were collected in the annulus section around the vapor inlet, which condensates were divided into an overhead liquid product stream 17 distilled off at a lower point of the annulus section and into an internal reflux stream 16 feeding back to the top of the column 13. The uncondensed vapors stream 15 was removed through the vapor outlet at the top of the HTM condenser 14. The overhead product stream 17 with a mass flow rate of 3,035 kg/h, greater than 85% by weight of L-lactide, was removed for further purification. The pressure drops caused by the HTM condenser 14 and the distillation column 13 were 1.7 mbar and 2.9 mbar, respectively, which pressure drops were added to give a total pressure drop of 4.6 mbar for the system. Setting the pressure of the vapor outlet stream 15 at 5 mbar by a vacuum system gave a pressure of 9.6 mbar for the evaporator 19 and the pot 18 during operation.

Example 3

400 kg/h of a purge stream 23 was fed to the wiped film evaporator 24. The vaporized components including crude lactide left the wiped film evaporator 24 via stream 26 to an external condenser 27, wherein the condensation took place. The condensate stream 29 had a mass flow rate of 360 kg/h and entered the overhead product stream 17. The uncondensed vapors were removed via stream 28. The least volatile component including the residues of tin catalyst and metals contaminants were removed via stream 25 for further process. The operating temperature and pressure of the wiped film evaporator 24 were set in the range of 200 to 230° C. and 6 mbar, respectively.

Example 4

A distillation of the main distillation with the side-draw refluxer according to an embodiment of the invention as shown in FIG. 1 was performed. The main distillation column 31 had a total of 35 theoretical stages and the side-draw refluxer 43 has a total of 6 theoretical stages. 3,550 kg/h of a feed at a temperature of 107° C. was continuously fed to the main distillation column 31 with the feed inlet located at the point of theoretical stage 9.

The HTM condenser 32 had a total of 360 tubes, each having a length of 4,000 mm and an OD of 25.4 mm. The shell ID of the HTM condenser 32 was 1,600 mm. The total surface area of the HTM condenser 32 was 110 $m^2$. The total pressure drop caused by the HTM condenser 32 was 1.6 mbar during operation.

The HTM condenser 44 had a total of 242 tubes, each having a length of 3,500 mm and an OD of 25.4 mm. The shell ID of the HTM condenser 44 was 1,100 mm. The total surface area of the HTM condenser 44 was 65 $m^2$. The total pressure drop caused by the HTM condenser 44 was 1.2 mbar during operation.

As described in the above examples according to the present invention, the use of a HTM condenser instead of a conventional condenser is particularly useful for reducing the total pressure drop of a system and thus decreasing the operating temperature of the system correspondingly. In addition, a wiped film evaporator is utilized for the removal of the metal contaminants contained in the purge stream and recovery of the crude lactide by depolymerization of the unconverted lactic acid oligomers contained.

The invention claimed is:

1. A continuous method for production of optically pure lactide from an aqueous solution of lactic acid, the method comprising:

feeding the aqueous solution of lactic acid to a first reactive distillation system to generate lactic acid oligomers;

feeding the lactic acid oligomers to a second reactive distillation system to generate crude lactide;

feeding the crude lactide to a main distillation system to purify the crude lactide and generate high purity lactide as a vapor side-draw; and feeding the vapor side-draw to a side-draw refluxer to obtain the optically pure lactide from the side-draw refluxer, wherein at least one of the first reactive distillation system, the second reactive distillation system, the main distillation system, and the side-draw refluxer is fitted with a horizontally top-mounted (HTM) condenser to give low pressure drops and thus reduce side-reactions associated with high bottom temperatures, wherein the HTM condenser comprises:— a cylindrical shell and a number of tubes mounted inside the shell;

a longitudinal baffle installed in the shell, separating an inner space of the shell into a tube layout section above and an empty section below the longitudinal baffle;

vertical single segmental baffles connected to the longitudinal baffle in the tube layout section;

a vapor inlet at a bottom of the HTM condenser for rising vapors; and an uncondensed vapor outlet at a top of the HTM condenser, wherein vapors enter the HTM condenser through the vapor inlet, are guided by the longitudinal baffle and the vertical single segmental baffles, and exchange heat with a cooling medium flowing inside the tubes, wherein vapor condensation takes place in an area created by the longitudinal baffle and the vertical single segmental baffles, wherein formed condensates flow across the longitudinal baffle into the empty section of the shell, and wherein uncondensed vapors are removed from the uncondensed vapor outlet.

2. The method of claim 1, wherein the first reactive distillation system comprises a distillation column, and wherein the HTM condenser is directly welded or connected to a top of the distillation column in the first reactive distillation system.

3. The method of claim 1, wherein the second reactive distillation system comprises a distillation column, and wherein the HTM condenser is directly welded or connected to a top of the distillation column in the second reactive distillation system.

4. The method of claim 1, wherein the main distillation system comprises a distillation column, and wherein the HTM condenser is directly welded or connected to a top of the distillation column in the main distillation system.

5. The method of claim 1, wherein the side-draw refluxer comprises a distillation column, and wherein the HTM condenser is directly welded or connected to a top of the distillation column in the side-draw refluxer.

6. The method of claim 1, wherein the longitudinal baffle has a slope of 3-7° and is installed in the middle of the shell, and wherein in the tube layout section, five vertical single segmental baffles are arranged, wherein two of the vertical single segmental baffles are separately connected to left and right ends of the longitudinal baffle, and the other three vertical single segmental baffles are installed between them.

7. The method of claim 1, wherein the HTM condenser has one shell pass for vapors to be condensed and multiple tube passes for the cooling medium.

8. The method of claim 6, wherein in the HTM condenser, the vapors entering the HTM condenser are guided by the longitudinal baffle and the five vertical single segmental baffles, and exchange heat with the cooling medium flowing inside the tubes.

9. The method of claim 6, wherein in the tube layout section of the HTM condenser, the vapor condensation takes place in the area created by the longitudinal baffle and the five vertical single segmental baffles, and to a lesser extent in the area outside the left and right ends of the longitudinal baffle.

10. The method of claim 6, wherein in the HTM condenser, most of the formed condensates flow across the longitudinal baffle into the empty section of the shell through the gap between the longitudinal baffle and the inner wall of the shell, and the rest of the formed condensates fall directly back to the empty space section from outside the left and right end of the longitudinal baffle.

11. The method of claim 1, wherein the HTM condenser comprises an annulus section around the vapor inlet for accumulation of condensates, an overhead liquid product outlet located at a lower point of the annulus section, and an internal reflux outlet located at a higher point of the annulus section.

12. The method of claim 1, wherein the HTM condenser has a pressure drop of less than 2 mbar during operation.

* * * * *